United States Patent
Maresca, Jr. et al.

(10) Patent No.: US 9,766,175 B1
(45) Date of Patent: Sep. 19, 2017

(54) METHOD AND APPARATUS FOR IN-SERVICE MEASUREMENT OF THE BOTTOM THICKNESS AND CORROSION RATE OF A TANK BOTTOM

(71) Applicant: Vista Precision Solutions, Inc., Richland, WA (US)

(72) Inventors: Joseph W. Maresca, Jr., Sunnyvale, CA (US); Brian E. Humann, Benton City, WA (US); Wendell G. Faultersack, Kennewick, WA (US); Wilhelmina C. Leuschen, Kennewick, WA (US)

(73) Assignee: Vista Precision Solutions, Inc., Richland, WA (US)

( * ) Notice: Subject to any disclaimer, the term of this patent is extended or adjusted under 35 U.S.C. 154(b) by 359 days.

(21) Appl. No.: 14/258,609

(22) Filed: Apr. 22, 2014

Related U.S. Application Data

(63) Continuation-in-part of application No. 14/061,484, filed on Oct. 23, 2013, and a continuation-in-part of application No. 13/786,316, filed on Mar. 5, 2013, now Pat. No. 9,228,932.

(60) Provisional application No. 61/814,786, filed on Apr. 22, 2013, provisional application No. 61/795,737, filed on Oct. 23, 2012, provisional application No. 61/634,786, filed on Mar. 5, 2012.

(51) Int. Cl.
| | |
|---|---|
| *G06F 19/00* | (2011.01) |
| *G01N 17/00* | (2006.01) |
| *G01N 29/14* | (2006.01) |
| *G01M 3/24* | (2006.01) |

(52) U.S. Cl.
CPC .............. *G01N 17/00* (2013.01); *G01M 3/24* (2013.01); *G01N 29/14* (2013.01)

(58) Field of Classification Search
CPC ..... G07C 5/008; A47L 2201/00; B01D 21/02; B01D 21/24
USPC .................................. 702/34, 182–185, 188
See application file for complete search history.

(56) References Cited

U.S. PATENT DOCUMENTS

| | | | |
|---|---|---|---|
| 4,918,989 A | 4/1990 | Desruelles et al. | |
| 5,231,866 A | 8/1993 | Peacock | |
| 5,854,557 A | 12/1998 | Tiefnig | |
| 2002/0043973 A1 | 4/2002 | Amini et al. | |
| 2005/0011278 A1 | 1/2005 | Brown et al. | |
| 2006/0010995 A1* | 1/2006 | Silverman ............ | G01N 29/225 73/865.8 |

(Continued)

*Primary Examiner* — Edward Raymond
(74) *Attorney, Agent, or Firm* — David H. Jaffer; Pillsbury Winthrop Shaw Pittman LLP

(57) ABSTRACT

A method and apparatuses to make an in-service measurement of the thickness and corrosion rate of the floor an aboveground or bulk underground storage tank. The preferred method is to use an off-the-shelf ultrasonic sensor that is placed on the end of a staff and inserted into an opening at the top of the tank to make one or more local measurements of the thickness and corrosion rate of the tank floor. When combined with the results of a previous out-of service internal inspection of the floor or an acoustic emission (AE) corrosion activity test performed with a vertical and horizontal array of three or more AE sensors placed on a staff and inserted into the liquid or on the external wall of the tank and show almost no corrosion activity, these local measurements can be used to determine the thickness and corrosion rate for the entire tank floor.

46 Claims, 12 Drawing Sheets

(56) References Cited

U.S. PATENT DOCUMENTS

2006/0169022 A1     8/2006   Sato et al.
2006/0283251 A1   12/2006   Hunaidl et al.
2011/0185814 A1     8/2011   Piccolo \* cited by examiner

METHOD AND APPARATUS FOR IN-SERVICE MEASUREMENT OF THE BOTTOM THICKNESS AND CORROSION RATE OF A TANK BOTTOM

RELATED APPLICATIONS

This application claims priority from U.S. Provisional Application Ser. No. 61/814,786 filed Apr. 22, 2013, and is (a) a continuation-in-part of U.S. patent application Ser. No. 14/061,484, filed Oct. 23, 2013, which claims priority from U.S. Provisional Patent Application Ser. No. 61/795,737 filed Oct. 23, 2012 and U.S. Provisional Patent Application Ser. No. 61/814,786 filed Apr. 22, 2013 and (b) a continuation-in-part of U.S. patent application Ser. No. 13/786,316 filed Mar. 5, 2013 (now U.S. Pat. No. 9,228,932), which claims priority from U.S. Provisional Patent Application Ser. No. 61/634,786 filed Mar. 5, 2012.

BACKGROUND OF THE INVENTION 1.0 Field of the Invention

The method and apparatuses of the present invention is to make in-service measurements of the thickness and corrosion rate of the entire floor of an aboveground storage tank (AST) or a bulk underground storage tank (UST) containing petroleum products, chemicals, or water using local or spot measurements of floor thickness and corrosion rate. These in-service measurements can be used in conjunction with tank integrity or leak detection measurements to determine the time interval to the next out-of-service internal inspection made in conjunction with API 653 and other similar practices.

2.0 Brief Description of Prior Art

There are several standards for inspecting the integrity of welded or riveted, atmospheric pressure, aboveground storage tanks (ASTs) after they have been placed in service. API 653 covers the maintenance inspection, repair, alteration, relocation, and reconstruction of such tanks (API 12R1 is similar to API 653 but is designed for production tanks). It is a performance-based inspection with the time between inspections being 10 years or more for out-of-service inspections and 5 years or less for in-service inspections. The scope of this API publication is limited to the tank foundation, bottom, shell, structure, roof, attached appurtenances, and nozzles to the face of the first flange, first threaded joint, or first welding-end connection. While it can be used for inspecting shop-fabricated tanks, it is mainly intended for field-erected ASTs. It is also used for many of the military's large, bulk underground storage tanks (USTs). In September 2000, the Steel Tank Institute (STI SP001) published a standard for inspection and repair of shop-fabricated steel tanks. The STI standard addresses double-wall tanks and tanks with integral secondary containment pans as well as horizontal tanks; none of these tanks are within the scope of API 653. This standard includes a risk-based approach to inspections, where tanks with the most risk requiring more frequent inspections. The risk-based approach is a function of the size, containment, release prevention and detection, and corrosion history of the tank.

In 1988, the U.S. Enviromnental Protection Agency (EPA) Code of Federal Regulations (CFR) 40 CFR Part 280 and 40 CFR Part 112 mandated industry standard inspections on tanks and piping that have the potential of impacting the environment as the result of a product release due to a leak or a tank or pipe failure. Each state has implemented this regulation with the EPA standards establishing the minimum requirements. Large, bulk underground and all aboveground storage tanks were excluded from the integrity parts of the regulation. Until recently, only a few states regulated the inspection of these large tanks for integrity. The Spills Prevention Controls and Countermeasures Program (SPCC) generally controls the inspection of petroleum facilities containing ASTs or bulk USTs. Recently, the guidelines for periodic inspection of these large tanks have become mandatory. The petroleum industry has been performing inspections on their tanks for many years, because it is the criterion by which a facility is judged when tank release or tank failure incidents occur.

API Recommended Practice 580 describes the elements of a risk-based approach to an inspection program. It provides the guidance for developing, implementing, and maintaining a risk-based inspection (RBI) program. The guidelines include the means for assessing the program and its plan, while emphasizing safe and reliable operations. The ultimate goal of an internal inspection is the safety and reliability of the operating facilities. A risk-based approach, which takes into account the probability of a failure and the consequence of a failure, can be used to set better intervals between inspections or the time to the next inspection. This approach acknowledges that it is important to focus the highest efforts and resources on address maintenance and repairs on those facilities needing it most. By focusing these efforts where they are needed most, more problems will be found earlier and the facilities will be operated safer and less expensively. A risk-based approach also saves money and a permits better use of the operational facilities, because they do not need to be taken out of service before it is necessary. The routine time interval, which has been the practice, can be very costly and may not result in less than optimal maintenance and repair. A risk-based approach will better prioritize and manage the tank inspection program. In two patent applications, Maresca et. al. teach methods and apparatuses for determining the time interval between inspections or to the next inspection.

In general, API 653 and most regulatory agencies require an out-of-service inspection every 10 years unless the tank is in good shape, the corrosion rate is low, and the minimum required thickness of the tank floor will not be exceeded. An out-of-service inspection is very expensive, not only because of the inspection itself, but the loss of the tank for operations during the inspection, repairs, and maintenance activities. The RBI methods of API 580/581 have been incorporated into the $4^{th}$ edition of API 653. Maresca et. al. teach methods and apparatuses that are in compliance with these standards for determining the time interval between inspections or to the next inspection. The method is comprised of a third-party evaluated leak detection test, one or more local measurements of the floor thickness and corrosion rate at one or more regions on the tank floor, and the results of an AE corrosion activity test showing little to no corrosion activity. If the tank is not leaking, then the floor has integrity and has remaining life. If the results of the AE corrosion activity test show little or no activity, then the local measurement of floor thickness and corrosion rate that can be assumed to be typical of the entire tank floor. The method and apparatuses of the present method describe one or more measurement approaches to implement these RBI methods used to determine the time between or to the next out-of-service internal inspection.

Regular in-service inspections are performed on most tanks. These inspections are typically conducted every 5 years and address the condition of the accessible portions of the tank. Visual inspection is a very important part of this process. UT measurements of the thickness of the shell are routinely made to insure the tank has sufficient wall thickness (i.e., strength) to support the product. Unfortunately, most problems occur in the tank floor where visual access is not possible without taking the tank out-of-service, removing the product from the tank, and cleaning the tank. As a consequence, the interval between tank inspections is typically set based on a schedule and/or the rate of corrosion estimated from a previous tank inspection and the minimum allowable thickness of the floor. More recently, risk assessment procedures have also been developed to determine this interval. Typically, the time interval between inspections is 10 years although longer intervals may be possible for tanks in good shape. The basic internal inspection procedure (API 653, API12R, or STI SP001) is designed to insure that the structure is in good shape (i.e., not corroding) with the walls, floor, and appurtenances having adequate thickness to structurally support tank operations until the next inspection. As stated above, API 653 and 580/581 have established the guidelines for implementing a tank inspection with the goal of establishing meaningful and cost-effective intervals for inspections. However, they have not specified methods or acceptable approaches. They acknowledge that tanks that have the potential for being in poor shape should be inspected more frequently than tanks in good shape. The difficulty has been to meaningfully assess the condition of the tank and to meaningfully set a safe inspection interval.

There have been a number of approaches for assessing the condition of the tank, for better prioritizing which tanks should be inspected first, and for safely and reliably extending the time between inspections.

The main methods used to justify extending the time between inspections have been AE methods. For example, a number of methods using the AE inspection method called TANKPAC™ by Physical Acoustics Corporation have been developed and evaluated. Up to 4 years are possible with these methods. Generally, 12 AE sensors are mounted on the external wall of an AST, and the data is collected and analyzed after a 24-h waiting period for the tank to become acoustically quiet. This method can be expensive to use and can require a high degree of technician skill to obtain accurate results. Furthermore, AE methods do not measure floor thickness and are not reliable as leak detection methods for determining the integrity of the floor. In addition, these methods are not always fully accepted in all circles. However, extensive field evaluations where full out-of-service internal inspections have followed such AE measurements, it is clear when certain results are obtained there is a very high probability that the tank is in good shape. If combined with a leak detection method and/or a local measurement of floor thickness, a strong basis for extending the interval between inspections is provided. These methods have been extensively used in many countries of the world. Other types of methods that assess the rate of corrosion from LRUT sensors placed on the outside wall floor have also been used. The main issue is that AE methods do not measure floor thickness and as a consequence, corrosion rates and floor thickness cannot be accurately evaluated (e.g., using Eq. (1)). However, the method of the present invention can utilize the strongest part of the test (i.e., when the AE system indicates no damage), the spatial distribution of the corrosion activity, and the leak detection capability as an element in the method that benefits greatly from actual floor measurements.

Loo [1999] reported on a study of 148 aboveground storage tanks inspected using an AE method (TANKPAC™) of assessing the corrosion activity in the floor of an aboveground storage tank while in-service. The AE results for each of these 148 tanks were compared to the results of an internal inspection of the tank floor performed as part of an out-of-service inspection. Of the 148 tanks, 33 were crude tanks and 115 were refined product tanks. The results were summarized in FIG. 2 of Loo's paper. The results of the internal inspections (i.e., the actual or true condition of the tank) were reported in terms of four categories (FU1, FU2, FU3, and FU4). The results of the AE tests, which were reported in terms of five corrosion grades from A to E (as defined below), were compared to the out-of-service inspection results. The definitions of the AE Test Results and the Out-of-Service Internal Inspections are given below:

| AE Test Results | Maintenance and Repair |
| --- | --- |
| A: Very minor | No maintenance necessary |
| B: Minor | No maintenance necessary |
| C: Intermediate | Some maintenance is needed |
| D: Active | Give priority in maintenance schedule |
| E: Highly active | Give highest priority in maintenance schedule |

| Out-of-Service Internal Inspection Results | |
| --- | --- |
| FU1: No damage/No repair | (A) |
| FU2: Minor damage/No repair | (B, some C) |
| FU3: Damage/Some repair | (D, some C) |
| FU4: Damage/Major repair/New floor | (E) |

As will be described below, there is some uncertainty on how to compare the results of the 5 AE Test Results with the four Internal Inspections, mainly with respect to Grade C and FU2 and FU3.

As described in Loo, the AE method is intended to distinguish tanks in need of maintenance or repair from those that do not and is a really considered a sorting technique as applied. Table 1 summarizes the results obtained from FIG. 2. The table illustrates some very important conclusions about (1) the overall condition of the tanks in the population and (2) the overall reliability of the AE method. Depending on the actual results of the AE test, it can be very reliable in supporting the tank assessment either as applied by Loo or as applied in the present invention. However, in general, our assessment of these results concludes that the AE method leads to correct decisions about the condition of the tank floor only 76.7% of the time with a probability of false alarm of 14.5% and a probability of missed detection of 8.8%. Even the correct decisions are not easy to determine because false alarms and missed detections happens for all grades except A.

When the results of the AE test indicate an A grade, there is a high level confidence that the rate of corrosion of the tank is low and no maintenance or repair of the tank is required. This accounted for 30.5% of the tanks evaluated, i.e., about 1 in 3 tanks tested. Furthermore, when the results of the AE test indicate a B grade, there is also a high level of confidence about the rate of corrosion being low with no maintenance or repair required, but at least 4, and up to 6, of the 41 tests results classified as a B grade are actually missed detections (i.e., tanks deemed as not needing maintenance or repair that do need maintenance or repair). It is difficult to determine how to interpret the C grade and the FU3 test results, because as defined the FU3 should be equated to a D grade, but the results tend to show many of the FU3 tests are C grades. In general, for our analyses in Table 1, we have assumed about half of the FU3 test results are missed detections and half would be included with the FU1,2 test results as we might expect from the definitions.

overall method. First, 64.2% of the tanks tested need little or no maintenance or repair. Thus, there is almost a 2 in 3 chance that any tank that passes a Leak Test is in good shape. Second, 14.2% of the tanks tested need significant maintenance or repair. Thus, a Leak Detection Test will correctly identify 78.4% of the tank conditions. This leaves 21.6% as uncertain with more information needed to ascertain their true condition. In general, we would expect that almost all of these 21.6% of the tanks would pass a Leak Detection Test even though they still need some repair and/or some maintenance. Thus, some measurement of the tank floor condition is needed in addition to the AE test.

TABLE 1

Summary of the AE Corrosion Activity Tests [Source: Loo, (1999)].

| AE Grade | % of Tanks | Number of Tanks | Cum % of Tanks | FU1/2 | FU3 | FU4 | | FU1/2 | FU3 | FU4 | |
|---|---|---|---|---|---|---|---|---|---|---|---|
| A | 30.5% | 45 | 30.5% | 100.0% | 0.0% | 0.0% | 100.0% | 45 | 0 | 0 | 45 |
| B | 27.5% | 41 | 58.0% | 76.0% | 14.0% | 10.0% | 100.0% | 31 | 6 | 4 | 41 |
| C | 25.0% | 37 | 83.0% | 38.5% | 48.5% | 13.0% | 100.0% | 14 | 18 | 5 | 37 |
| D | 7.5% | 11 | 90.5% | 18.5% | 45.0% | 36.5% | 100.0% | 2 | 5 | 4 | 11 |
| E | 9.5% | 14 | 100.0% | 21.0% | 21.0% | 58.0% | 100.0% | 3 | 3 | 8 | 14 |
| | 100.0% | 148 | | | | | 500.0% | 95 | 32 | 21 | 148 |
| | | | | | | | | 64.2% | 21.6% | 14.2% | 100.0% |

| AE Grade | Correct Decision | | Incorrect Decision | | False Alarms | | Missed Detections | |
|---|---|---|---|---|---|---|---|---|
| A | 45 | 100.0% | 0 | 0.0% | 0 | 0.0% | 0 | 0.0% |
| B | 31 | 75.6% | 10 | 24.4% | 10 | 24.4% | 0 | 0.0% |
| C | 23 | 62.2% | 14 | 37.8% | 9 | 24.3% | 5 | 13.5% |
| D | 6.5 | 59.1% | 5 | 40.9% | 3 | 22.7% | 2 | 18.2% |
| E | 8 | 57.1% | 6 | 42.9% | 0 | 0.0% | 6 | 42.9% |
| | 114 | 76.7% | 35 | 23.3% | 22 | | 13 | |
| | | 76.7% | | 23.3% | | 62.3% | | 37.7% |

Five of the D and E grades were actually assessed as FU1, 2 tanks and were judged to be in very good condition, i.e., false alarms. Ten of the tests graded as a B were actually assessed as FU3 and FU4 where damage has occurred, i.e., missed detections. Thus, how the AE test results are used in the method of the present invention is very dependent on the actual results of the AE test. More reliability can be assigned to the AE test results when a local UT floor thickness measurement is used to help interpret the results. Also, more reliability can be assumed if additional advanced signal processing method is used to determine the grade.

As stated above, strong statements can be made when an A or B grade is determined, particularly for an A grade. This is not the case for D and E grades, because there are almost as many tanks in need of maintenance or repair as prescribed by FU4 that receive a B or C grade vice a D or E grade. If the AE test results indicate a problem, you would be correct only 38.1% of the time. Similarly, if the AE results were A, B, or C, you would miss 9 of the 123 tanks (7.3%) in need of serious maintenance and repair and possibility more if the tanks with a C grade need some repair. Thus, we would consider the results of a previous API 653 inspection to be more reliable than a, current AE inspection if the results of the AE test were D or E.

Some general conclusions about the condition tanks in general can be made from Table 1, which can support the Cole and Gautrey [2002] described history of the AE method used in the Loo study and included additional data and illustrations of the use of the method for ascertaining the condition of a tank and whether or not the time between scheduled internal inspections can be extended. Their FIG. 10 increased the number of tanks used in Table 1 from 148 to 157; the results were very similar. In their FIG. 11, they reported the results of a similar study by the French Institute of Petroleum for a sample population of 78 tanks with very similar results. Table 2 compares the results from Loo, Cole and Gautrey, and the French Institute of Petroleum and shows that they are very similar. The main conclusions hold: (1) tanks with AE reported grades of A and B (FU1,2) show very little or some maintenance and repair required, (2) tanks with AE reported grade of D and E showed large damage (FU4) with a high degree of maintenance and repair needed, (3) a small number of false alarms in which AE reported grades of D and E were actually in good shape (FU1,2) or not in very bad shape (FU3), and (4) no missed detections in which tanks in very bad shape (FU4) were reported in good shape. The strongest statements that can be made about the AE test is that if a test results in a grade of A or B, it should be in good shape. Conversely, if a tank is reported with a grade of D or E, it should be treated as such even though about half of the tanks in this category were actually in moderate to good shape.

TABLE 2

Summary of the AE Corrosion Activity Test Results from Three Sources.

| AE Grade | Loo (1999): 148 Tanks | | | French Institute of Petroleum (2002): 78 Tanks | | | Cole and Gautrey (2002): 157 Tanks | | |
|---|---|---|---|---|---|---|---|---|---|
| | FU1/2 | FU3 | FU4 | FU1/2 | FU3 | FU4 | FU1/2 | FU3 | FU4 |
| A | 100.0% | 0.0% | 0.0% | 100.0% | 0.0% | 0.0% | 100.0% | 0.0% | 0.0% |
| B | 76.0% | 14.0% | 10.0% | 89.0% | 11.0% | 0.0% | 80.5% | 11.5% | 8.0% |
| C | 38.5% | 48.5% | 13.0% | 22.0% | 18.0% | 60.0% | 36.0% | 40.0% | 24.0% |
| D | 18.5% | 45.0% | 36.5% | 19.0% | 29.5% | 51.5% | 15.0% | 45.0% | 40.0% |
| E | 21.0% | 21.0% | 58.0% | 3.0% | 14.0% | 92.0% | 12.0% | 26.0% | 62.0% |

Mejia, Hay, Mustafa, and Santa Fe [2009] described a method of using AE to extend the time between scheduled inspections. Their Tables 2 and 3 summarize the application of their method, which combines the Overall Corrosion Grade A through E with a Potential Leak Detection Grade. The Potential Leak Detection Grade indicates areas of highly concentrated clusters of AE events, where five indicate very high potential and one indicates very low potential. Unlike the present method of this invention, this method does not specifically test for a leak. Table 3 summarizes their results. The schedule for an internal inspection can be postpone up to 4 years for A, B and 1, 2 grades, up to 2 years for C, D, E and 1 and most 2 grades, as well as A, B and 1, 3, 4 grades. A postponement of 0.5 and 1 year is possible for all but D, E and 5 grades. The method of the present invention allows extensions up to 5 years and has more reliability in the decision process, because the present method is based on whether or not a tank is leaking as determined from a Leak Detection Test and what the thickness and corrosion rate of the floor is from actual measurements. The data from the AE test as included in the method of the present invention can also be used to test the tank floor for leaks.

TABLE 3

Summary of the AE Corrosion Activity Test Interpretation in terms of the number of years extension for a potential leak grade and a Corrosion grade [Source: Mejia, Hay, Mustafa, and Santa Fe (2009)].

| Potential Leak Grade | Overall Corrosion Grade | | | | |
|---|---|---|---|---|---|
| | A | B | C | D | E |
| 1 | I | I | II | N/A | N/A |
| 2 | I | I | II | N/A | N/A |
| 3 | II | II | III | III | N/A |
| 4 | II | III | III | IV | IV |
| 5 | III | III | IV | IV | IV |
| 1 | 4 | 4 | 2 | N/A | N/A |
| 2 | 4 | 4 | 2 | N/A | N/A |
| 3 | 2 | 2 | Schedule | Schedule | N/A |
| 4 | 2 | Schedule | Schedule | Schedule | Schedule |
| 5 | Schedule | Schedule | Schedule | Schedule | Schedule |

I: Extension Time Interval = 4 years
II: Extension Time Interval = 2 years
III: Extension Time Interval = 1 years
IV: Extension Time Interval = 0.5 years
* or 6 months or 1 Year The method and apparatuses of the present invention is to provide and combine the results from an in-service, simple-to-use and effective bottom thickness sensor and an in-service, simple-to-use and effective AE sensor suite to determine the corrosion activity in the bottom or floor of an AST or bulk UST without taking the tank out of service. These measurements will be used the methods taught by Maresca, et. al. to implement a risk-based internal inspection to determine the time interval between or the time to the next out-of-service internal inspection.

SUMMARY OF THE INVENTION

It is the object of this invention to provide a method and apparatuses for safely measuring the thickness of the floor of an aboveground storage tank (AST) or a bulk underground storage tank (UST) without taking the tank out of service.

It is the object of this invention to provide a method and apparatuses for inserting and using an ultrasonic (UT) steel plate thickness sensor into the tank filled with liquid product to measure the thickness of the tank bottom or floor in a small local region in the tank.

It is the object of this invention to provide a method and apparatuses for using an ultrasonic (UT) sensor on a specially designed staff to be inserted into the tank for measurements of the floor when the staff may not be perpendicular to the floor.

It is the object of this invention to provide an in-service method and apparatuses for safely determining the level of corrosion in an aboveground storage tank (AST) or a bulk underground storage tank (UST) without taking the tank out of service using a vertical and horizontal array of acoustic emission (AE) sensors mounted on the external shell of the tank.

It is the object of this invention to provide a method and apparatuses for safely determining the level of corrosion in an aboveground storage tank (AST) or a bulk underground storage tank (UST) without taking the tank out of service using a vertical and horizontal array of acoustic emission (AE) sensors mounted on a staff that is inserted into product of the tank or suspended from a wire and mount in the tank product.

It is the object of this invention to provide a method and apparatuses for determining the floor thickness the corrosion rate throughout the entire tank floor using the local bottom thickness measurement of thickness and corrosion rate determined from a UT sensor and an AE sensor system, where the AE sensors may be inserted into the product or attached the external shell of the tank.

It is the object of this invention to provide a method and apparatuses for computing the time between or to the next internal, out-of-service inspection using the results of a leak detection test and floor thickness and corrosion measurements made with a UT floor thickness and AE sensors.

It is the object of this invention to provide a method and apparatuses for computing the time between or to the next internal, out-of-service inspection using the results of a leak detection test and floor thickness and corrosion measurements made with a UT floor thickness sensor and a previous out-of-service floor inspection like that performed in accordance with API 653.

It is the object of this invention to provide a method and apparatuses for computing the time between or to the next internal, out-of-service inspection using the results of a leak detection test and floor thickness and corrosion measurements made with a UT floor thickness sensor, AE sensors, and a previous out-of-service floor inspection like that performed in accordance with API 653.

A method and apparatuses is described to make an in-service measurement of the thickness and corrosion rate of the floor an AST or a bulk UST. The preferred embodiment uses a local measurement of the thickness and corrosion rate at one or a few locations in the tank and the results of an AE corrosion activity test showing little or no active corrosion activity together to extend the local measurements of the bottom or floor thickness to the entire tank bottom or floor. Alternatively, a previous out-of-service internal inspection of the tank floor or a previous robotic inspection of the tank floor can be used in place of or combined with the AE corrosion activity test to extend the local measurements of floor thickness and corrosion rate to the entire tank floor. The preferred embodiment of the method is to combine and insert three AE sensors on a staff with a UT sensor mounted on the bottom of the staff (or another staff) into the liquid product in the tank. Two of the AE sensors are mounted along the long axis of the staff inserted into the tank and the third AE sensor is at the same elevation as and perpendicular to one of the AE sensors on the staff and preferably the AE sensor nearest the bottom of the tank. The local UT measurement of floor thickness and floor corrosion rate (based on the loss of floor thickness since the last out-of-service internal inspection) is representative of the thickness and corrosion rate throughout the tank if the results of the AE corrosion activity test indicate little or no corrosion activity. If a previous internal inspection of the entire tank floor is available, the thickness and corrosion rate measured previously can be updated with the current measurement.

IN THE DRAWINGS

FIG. 9 illustrates a close-up of top of reader head showing reach arm connection and sensor cable pass-through.

DESCRIPTION OF THE PREFERRED EMBODIMENT

Figure 1:
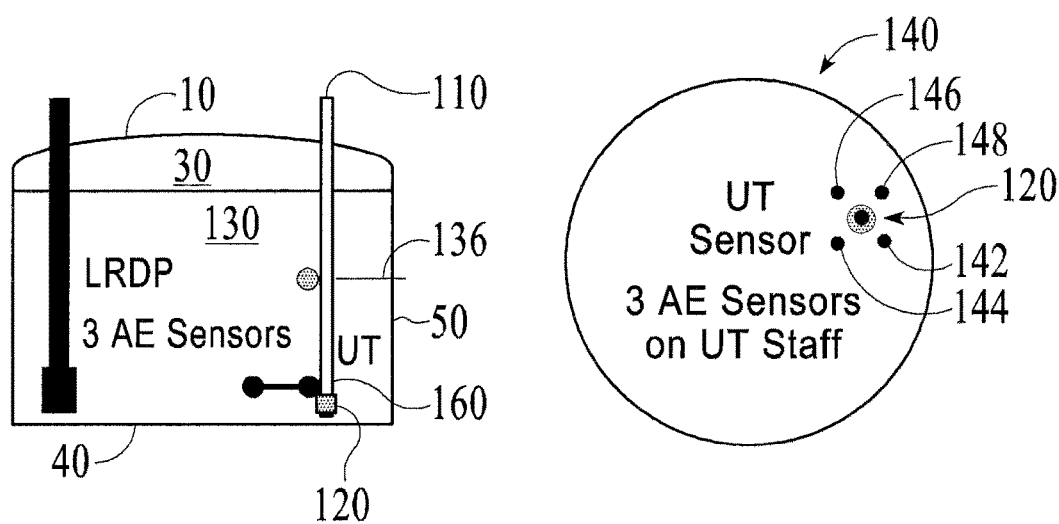
FIG. 1 illustrate an overview of UT and AE Corrosion Activity Test sensor suite with the AE sensors mounted on the inside of the AST and submerged in the liquid product.

A method and apparatuses is described to make an in-service measurement of the thickness and corrosion rate of the floor an AST or a bulk UST. This method and the apparatuses are used in conjunction with a leak detection system to determine the time interval between or to the next out-of-service internal inspection of the tank bottom or floor. The preferred embodiment uses a local measurement of the thickness and corrosion rate at one or a few locations in the tank and the results of an AE corrosion activity test showing little or no active corrosion activity together to extend the local measurements of the bottom or floor thickness to the entire tank bottom or floor. Alternatively, a previous out-of-service internal inspection of the tank floor can be used in place of or combined with the AE corrosion activity test to extend the local measurements of floor thickness and corrosion rate to the entire tank floor. The preferred embodiment of the method is to combine and insert three AE sensors on a staff with a UT sensor mounted on the bottom of the staff or on a separate staff into the liquid product in the tank. Two of the AE sensors are mounted along the long axis of the staff inserted into the tank and the third AE sensor is at the same elevation as and perpendicular to one of the AE sensors on the staff and preferably the AE sensor nearest the bottom of the tank. Alternatively, the AE sensors can also be submerged in the tank by suspending the AE sensors from a wire or they can be mounted on the outside shell of the tank with epoxy or a magnetic means, where at least two of the sensors are mounted horizontally and two are mounted vertically. The local UT measurement of floor thickness and floor corrosion rate (based on the loss of floor thickness since the last out-of-service internal inspection) is representative of the thickness and corrosion rate throughout the tank if the results of the AE corrosion activity test indicate little or no corrosion activity. Any type of sensor can be used to measure floor thickness. For example a magnetic flux sensor can be used to measure the thickness after being inserted into the tank or a Long Range Ultrasonic Technology (LRUT) can be used to measure the floor thickness in floor regions near the external shell of the tank. If a previous internal inspection of the entire tank floor is available, the minimum thickness and maximum corrosion rate determined in the previous internal inspection and updated for the entire tank floor by the ratio of the current local measurement of thickness and corrosion rate and the thickness and corrosion rate made in close location proximity to the current local measurements from the previous internal floor inspection. A previous robotic inspection of the tank floor where the thickness and corrosion rate of the floor was measured can be used as an alternative to a previous internal inspection of the tank floor.

A vertical and horizontal array comprised of three or more AE sensor are either placed on the external wall of the tank or on a staff suspended within the liquid. The UT sensor is packaged at the end of a staff and inserted into the tank from the roof of the tank. The head of the UT sensor will rotate so that solid contact with the tank floor is made even when measurements are not perpendicular to the floor (i.e., a minimum of 20 degrees). Both laboratory and field tests have been used to demonstrate the system. The UT sensor will measure floor thickness on a steel plate, a steel plate with holes, a steel plate that is rough and has grooves, and on a steel plate that has a coating. The UT sensor allows for the swivel mechanism to not be encumbered by the cable slack in the UT sensor regardless of line length required for the extended reach.

FIG. 1 illustrates the preferred method and apparatus of the present invention whereby the AE sensor array 130 is placed in and submerged in the liquid product 130 in the tank 10. The floor thickness measure sensor 120 is positioned on the bottom of a pole or staff 110 and the bottom thickness measurement sensor is positioned on the floor 40 or in close proximity to the floor 40 to measure the thickness of the floor plate 40 at that location. The floor thickness sensor 120 can be used to make a number of independent measurements of floor thickness (e.g., 140, 142, 144, 146, 148). Three to five independent measurements of thickness should be made so that the mean, median, and standard deviation can be computed. One measure 140 will suffice but 3 to 5 measurements insures that the first measurement is valid. We would expect the mean and the median to be approximately the same and the minimum or maximum thickness measurement to be within three standard deviations of the mean. If not the measurement should be repeated.

Figure 2:
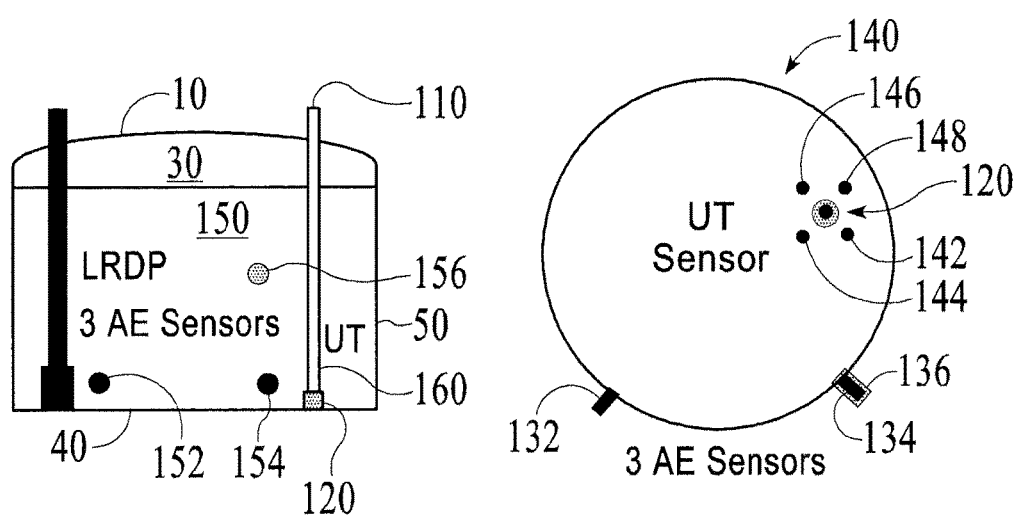
FIG. 2 illustrates an overview of UT and AE Corrosion Activity Test sensor suite with the AE sensors mounted on the outside wall of the AST.

While FIGS. 1 and 2 illustrate that the bottom thickness measurement is mounted on the end of a staff, the bottom thickness measurement sensor can be weighted and dropped into position from the top of the tank using a wire. The bottom thickness measurement sensor can also be inserted and dropped into position from the top of the tank using a wire and a magnetic means, where the magnetic can be attached to the face of the thickness measurement sensor or in an external arrangement that hold the sensor against the steel plate using magnetic place around the sensor.

Three or more AE sensors 132, 134, 136 are placed on a mounting pole or staff 110, which may be the same or a different staff 110 where the bottom thickness sensor is mounted. At least two of the AE sensors 132, 134 are mounted on a horizontal arm 160 that falls drops from a vertical position parallel to the staff 110 to a perpendicular for the in-tank measurements. These two sensors can be used to locate the position of an impulsive corrosion activity event emanating from active corrosion of the floor, but with a left-right ambiguity. These two AE sensors cannot distinguish a corrosion activity impulse emanating from the floor from an impulse emanating from the surface like that produced by a drop of liquid hitting the surface. This requires the use of an AE sensor mounted at a different vertical elevation 136 that the two AE sensors 132, 134 mounted in a plane horizontal to the tank floor. With a vertical array, either AE sensors 134, 136 or AE sensors 132, 136, impulsive signal produced on the floor can be distinguished from impulsive signals produced on the surface by their time of arrival.

If a third AE sensor 138 is positioned at another location in a horizontal plane with the two AE sensors 132, 134 mounted parallel to the floor, then an unambiguous time of arrival and floor location can be determined. For ease of analysis and mounting, AE sensor 138 should be 90 degrees from the line running through AE sensors 132, 134 and perpendicular to the staff 110. An unambiguous location of the impulsive signal emanating from the floor can also be determined if the vertical AE sensor 136 is not located in a plane with the horizontally positioned AE sensors 132, 134. This can be achieved by placing the vertical AE sensor 136 on an arm that drops vertically from the staff and is positioned perpendicular to the staff 110 and parallel to the floor for the in-tank AE measurements. Any position of the three AE sensors where only two AE sensors are in the same plane will allow unambiguous location estimates. As used, the ambiguity in the location of the three submerged AE sensors 132, 134, 136 will work fine for this method. The only reason to locate an impulsive corrosion signal on the floor is for quality control to validate that the signal is real. The exact location is not needed to determine that there is little or no active corrosion activity floor occurring on the floor.

FIG. 1 illustrates an in-tank leak detection method like Vista Precision Solutions LRDP mass-measurement leak detection system that is used to determine the integrity of the tank. A PASSing result indicates that there are no holes in the floor of the tank. When combined with a local measurement of floor thickness and the corrosion rate, an assessment of the remaining life of the tank can be estimated using the methods in Maresca, et. al. The corrosion rate is computed by differencing the thickness of the steel plate at the last internal inspection (or initial thickness of the tank for a new tank) and dividing by time between floor thickness measurements. This is accomplished by developing a life expectancy probability distribution of the tank and updating this distribution using a Bayesian calculation given that the tank has integrity, i.e., life, at the time of the leak detection test.

A wide variety of AE sensors can be used for this corrosion activity measure provided they have a frequency response ranging from 0 to 400 kHz and have sufficient signal to noise ratio (SNR) to detect the time of arrival of the corrosion activity impulsive signals. This can be determined from a number of calibration tests. One test is to break a number 9 pencil lead on the external wall of the tank and measure the SNR of the impulsive signal measured by the AE sensors. Another is to use a mechanical clicker, which is submerged in the liquid product to generate an impulsive signal. For best results the clicker signal should be produced near the bottom of the tank.

Figure 3:
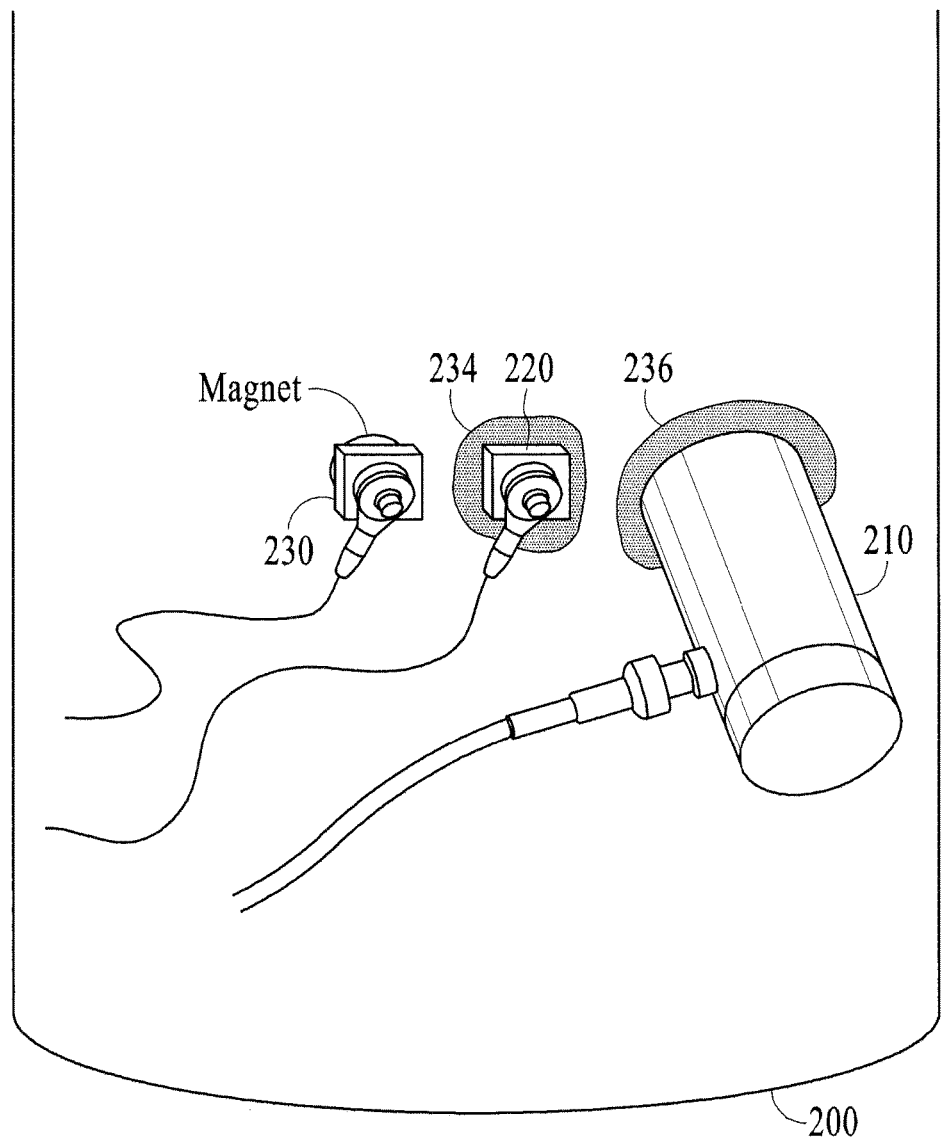
FIG. 3 illustrates an overview of UT and AE Corrosion Activity Test sensor suite with the AE sensors mounted on the outside wall of the AST. The AE sensor on the left is attached to the wall with a magnet.
Figure 4:
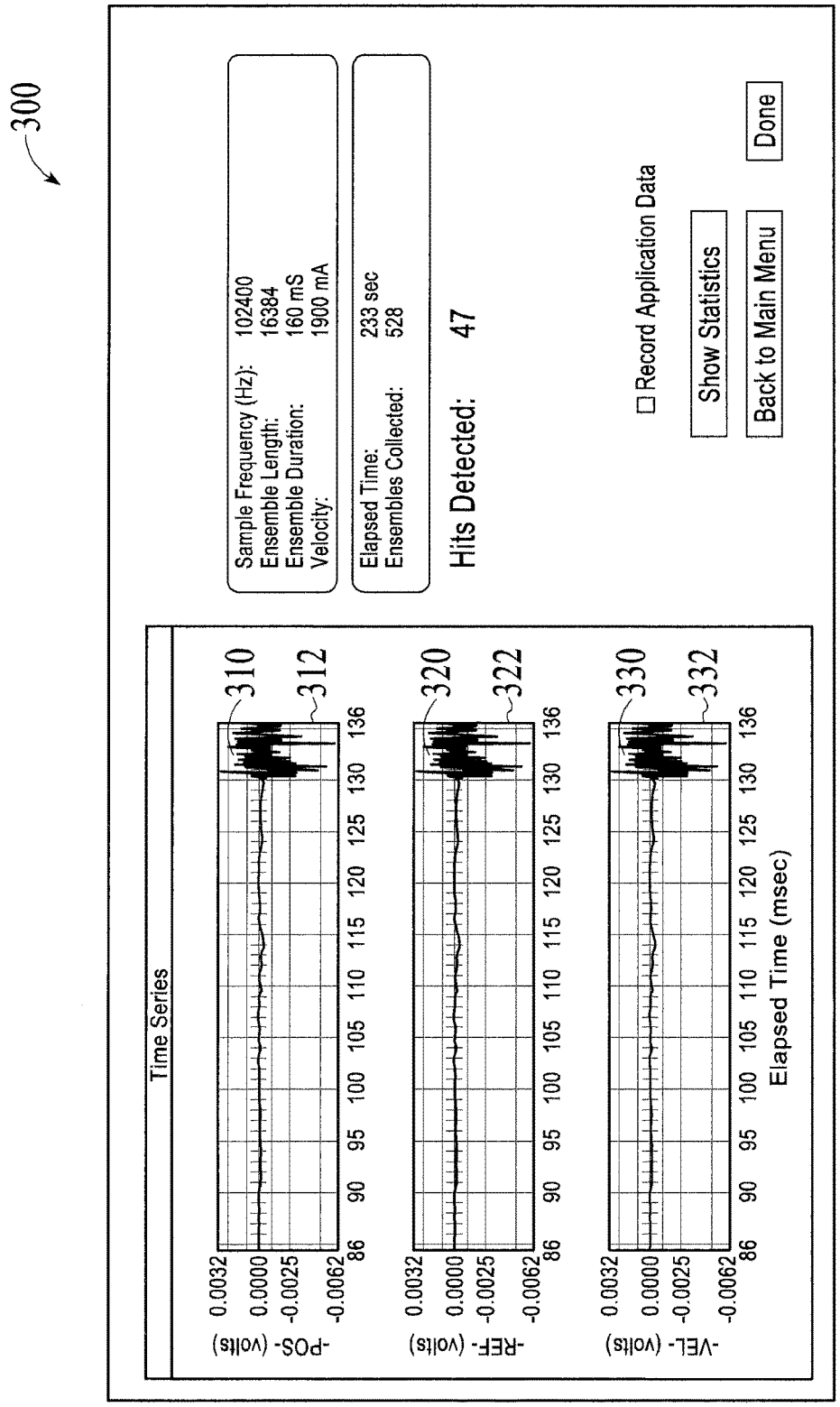
FIG. 4 illustrates the output of the three AE Corrosion Activity Test AE sensors.
Figure 5:
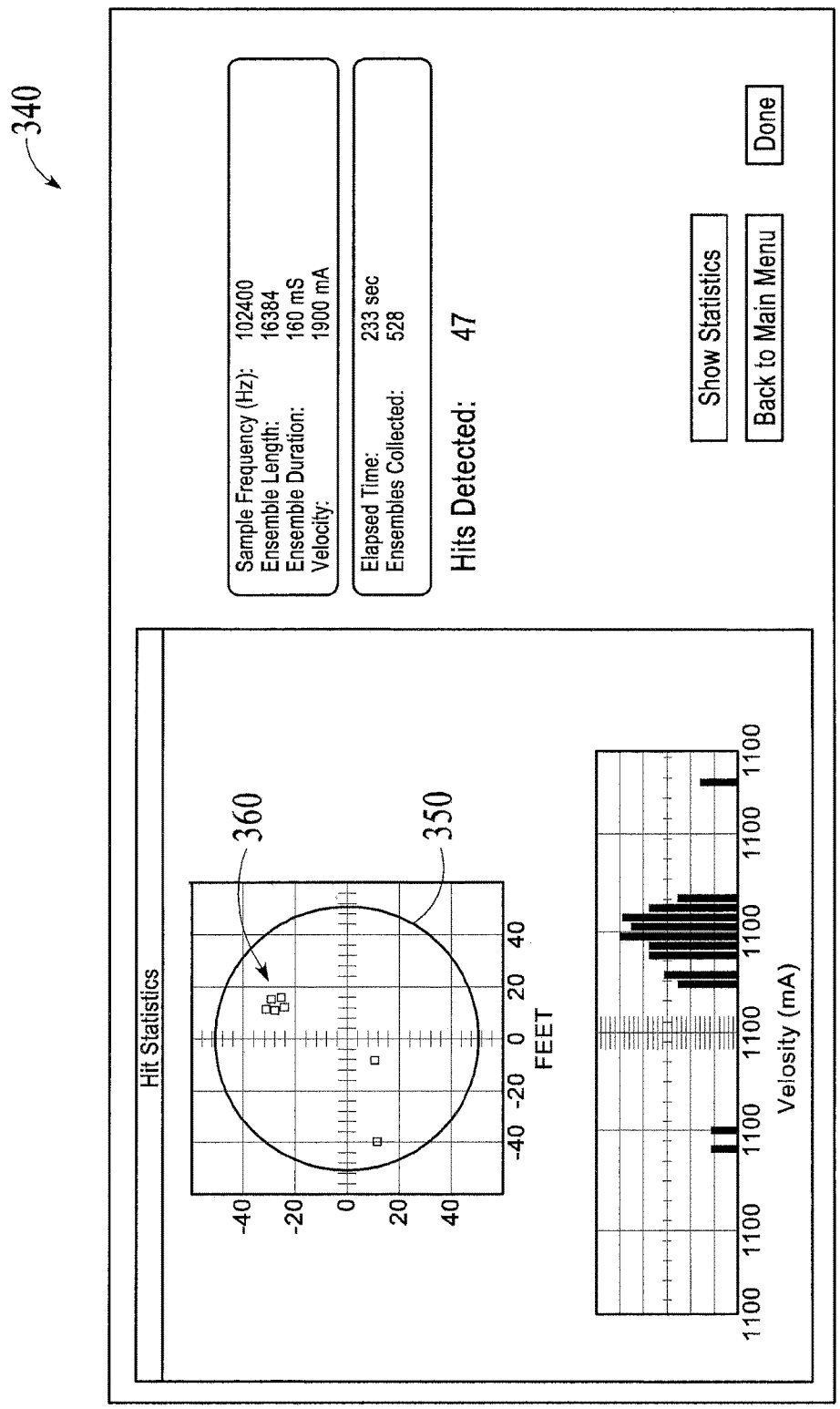
FIG. 5 illustrates an output of the corrosion activity and the velocity of the calibration signal using the AE Corrosion Activity Test Sensors.

FIGS. 3 through 5 illustrate some of the AE sensors that can be used and also show a typical output from the software used to process the corrosion signals and an output of the location of the corrosion signals. FIG. 3 illustrates two types of acoustic sensors 210, 220/230 and two of many different methods of mounting the sensors, one with a magnet 232 mounted to the bottom of the AE sensor and the other two AE sensors mounted on the wall of the tank 200 with epoxy 232, 236.

FIGS. 4 and 5, illustrates several of a number software outputs 300, 340 of a AE corrosion activity test. FIG. 4 illustrates the time of arrive of the impulsive acoustic signal produced near the bottom of the tank 350 (in FIG. 5) with a mechanical clicker. FIG. 5 illustrates the location 360 of the acoustic signal based on over 40 signals detected. FIG. 5 also illustrate a histogram of the measured velocity determined from the time of arrival and known location of the mechanical clicker and the AE sensors.

The time of arrival of the corrosion activity impulsive signals is processed automatically by first processing only the arrival of impulsive signals produced by the same corrosion activity event and then measuring the time of arrival of the leading edge of each impulsive signal by determining when a threshold is exceeded from (1) a running or block average of the standard deviation of the amplitude fluctuations of the impulsive time series using 3 or more data points, (2) a miming or block average of the mean or median of the raw amplitude fluctuations of the impulsive time series using 3 or more data points, (3) using the raw amplitude fluctuations of the impulsive time series, and/or (4) a miming or block average of (1) over more data points. The threshold is set so that none of background noise leading into the impulsive fluctuation produced by the corrosion event are large enough to exceed the threshold in (1) through (4). The threshold can be establish using time series of only background data when no impulsive signals due to a corrosion event are present or by find the approximate leading edge of the impulsive fluctuation produced by the corrosion event and determining the threshold from the background fluctuations leading into the leading edge. This processing is possible because the time series of a set duration are collected and they will only contain one impulsive signal if a corrosion event is present. The mixing of two or more impulsive signals from different corrosion event is eliminated because once any of the AE sensors detect the presence of an impulsive signal, a time window is then used to look for one and only one impulsive signal in the other AE sensors. The time window is long enough to allow the impulsive signal that is produced anywhere on the tank floor to reach all of the AE sensors. If more than one impulsive signal is detected in any of the time AE sensor time series, these data are not used.

The bottom thickness measurement sensor is preferably an ultrasonic (UT) thickness measurement sensor. This sensor should be place in contact with the floor of the tank. The thickness of the steel floor can be determined even if the steel plate is coated or lined. If sediment or sludge are present, then the such sediment or sludge should be removed before the measurement is made. This can be accomplished with a jet of fluid or by brushing the bottom, or by manipulating the probe until solid contact with the steel plate is achieved.

Other in-tank bottom thickness measurement sensor systems can be used. Off-the-shelf magnetic flux sensors can also be used. This type of sensor has the advantage that it does not necessarily need to be place directly on the surface of the floor and can make a thickness measurement while positioned slightly above the floor. External floor thickness measurements can also be used if they meet the precision and accuracy required for the thickness and corrosion rate measurements. One illustration is the LRUT system placed on the outside edge of the floor to measure the thickness of the floor near the outside circumference of the floor.

FIG. 2. illustrates an alternative embodiment of the present invention whereby the AE sensor system 150 is placed on the external wall or shell 50 of the tank 10. AE sensors 152 and 154 are located parallel to the floor and AE sensor 156 is located above AE sensor 154 to distinguish surface-derived impulsive events from impulsive floor corrosion events. Again, any configuration of AE sensors will work. In most traditional AE inspections, 12 AE sensors are mounted on the external shell of the tank and positioned in equally spaced intervals near the bottom and around the circumference of the tank. Any two of the AE sensors can be used to locate the source of the impulsive signal produced by a corrosion event if they have the range. The additional AE sensors insure that an impulsive signal occurring anywhere is the tank floor is detected and provide for more accuracy by having multiple triangulations possible. This is not necessary for these impulsive signals because they are much greater than the background fluctuations. The three AE sensors submerged in the tank and near the center of the tank would have about the same range response as the 12 AE sensors place around the circumference of the tank if the impulsive signal is adequately detected at a range equal to the radius of the tank. Unlike the two in-tank AE sensors 132, 134, the two external AE sensors 152, 156 do not have any ambiguity on the location of an impulsive signal.

To reiterate, for both AE sensor arrays illustrated in FIGS. 1 and 2, the vertically space sensors can be used to determine if the acoustic sounds are coming from the bottom as corrosion or leaks and not from the top as condensation. The horizontal sensors are used to determine the location of the corrosion activity event on the floor; the preferred configuration of the internal sensor array has a left right ambiguity, which is not present in the external array. The triangulation that can be done to locate the corrosion activity is only done for quality control and not for determining where the corrosion emanates. The main result is that no corrosion activity is heard. Thus, the location estimates are made only to verify that the corrosion signals are real and coming from within the tank. The time-interval window is used to insure that all of the AE sensors are seeing the impulsive signal from a single corrosion activity event. A third horizontal AE sensor positioned on the internal array 138, preferably in the plane of the bottom horizontal sensors and at right angles, can be used to eliminate the ambiguity in the submerged AE sensor system.

FIGS. 6-11 illustrate the UT sensor designed to measure the thickness of the floor at whatever the angle the staff is inserted into the tank or to make additional floor thickness measurements at short distances from the vertical position without directly overlapping the previous measurements. A summary of some of the key features comprising the UT sensor system are:

The UT sensor system can reach into a storage tank from the top to the bottom of the tank.

The invention can operate regardless of fill level of tank.

The invention can operate through a minor collection of sedimentation on the tank bottom.

The invention can operate on non-level tank bottoms.

The invention can be assembled in the field as part of insertion into the tank.

The invention is compatible function with a large range of products commonly stored in storage tanks.

The invention is intrinsically safe.

The invention is quick draining of product that ingress into the device during operation.

The invention has a safety retrieval line in event of hardware failure.

The invention is operated, assembled, and disassembled by hand without special tools.

Figure 6:
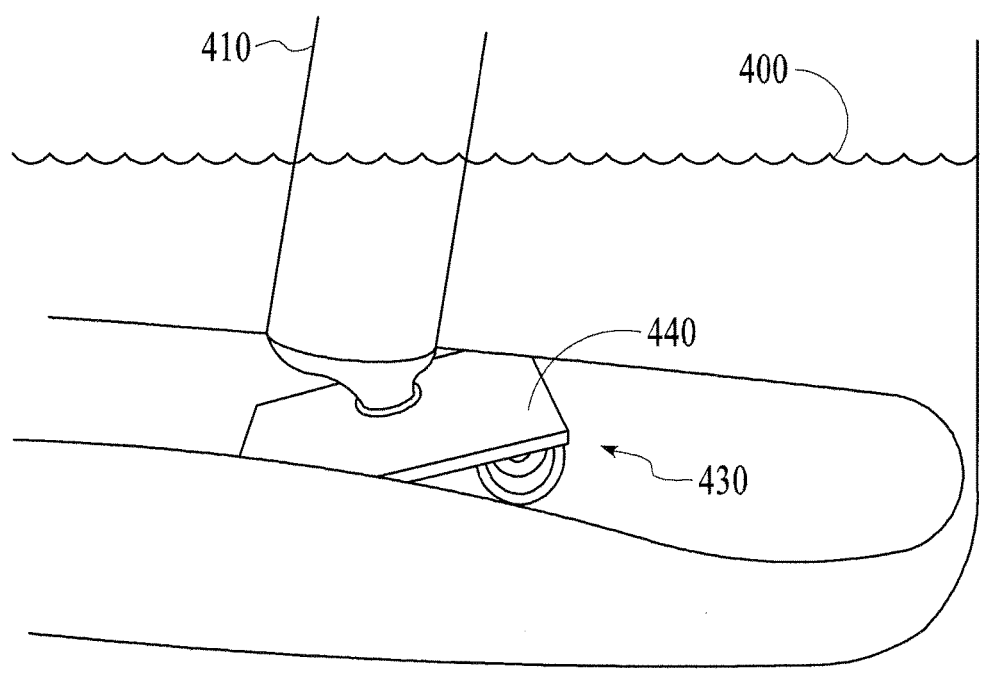
FIG. 6 illustrates a close-up of reader head during operation.

A summary of FIGS. 6-11 is provided below:

The photograph in FIG. 6 illustrates a close-up of the bottom of the UT sensor system 410 with a UT probe head 430 taking a measurement in a container of water 400 on steel coupon 440 of known thickness and place at an angle the vertical or staff 410. The reader head of the UT probe 430 in direct contact with the angled coupon 440 because of the swivel joint 420 located just above the head of the UT probe 430.

Figure 7:
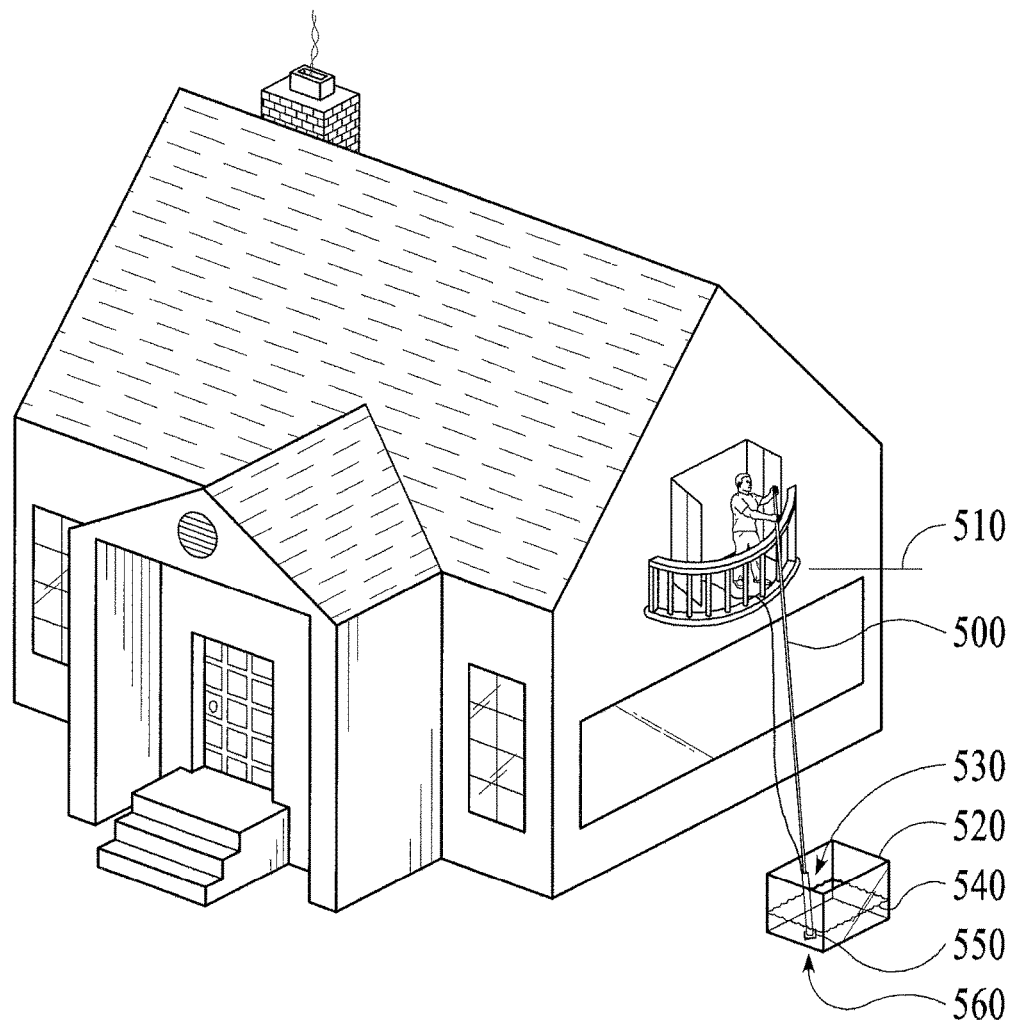
FIG. 7 illustrates the operation of making a UT measurement showing extended reach while operating in liquid.

The photograph in FIG. 7 illustrates making a measurement from elevated position 510 using a pole or staff 500 with the UT sensor 530 mounted on the bottom of the staff 500 and inserted into a container 520 of water 540 with the head of the UT probe 550 in direct contact with the steel coupon 560 located on the bottom of the container.

Figure 8:
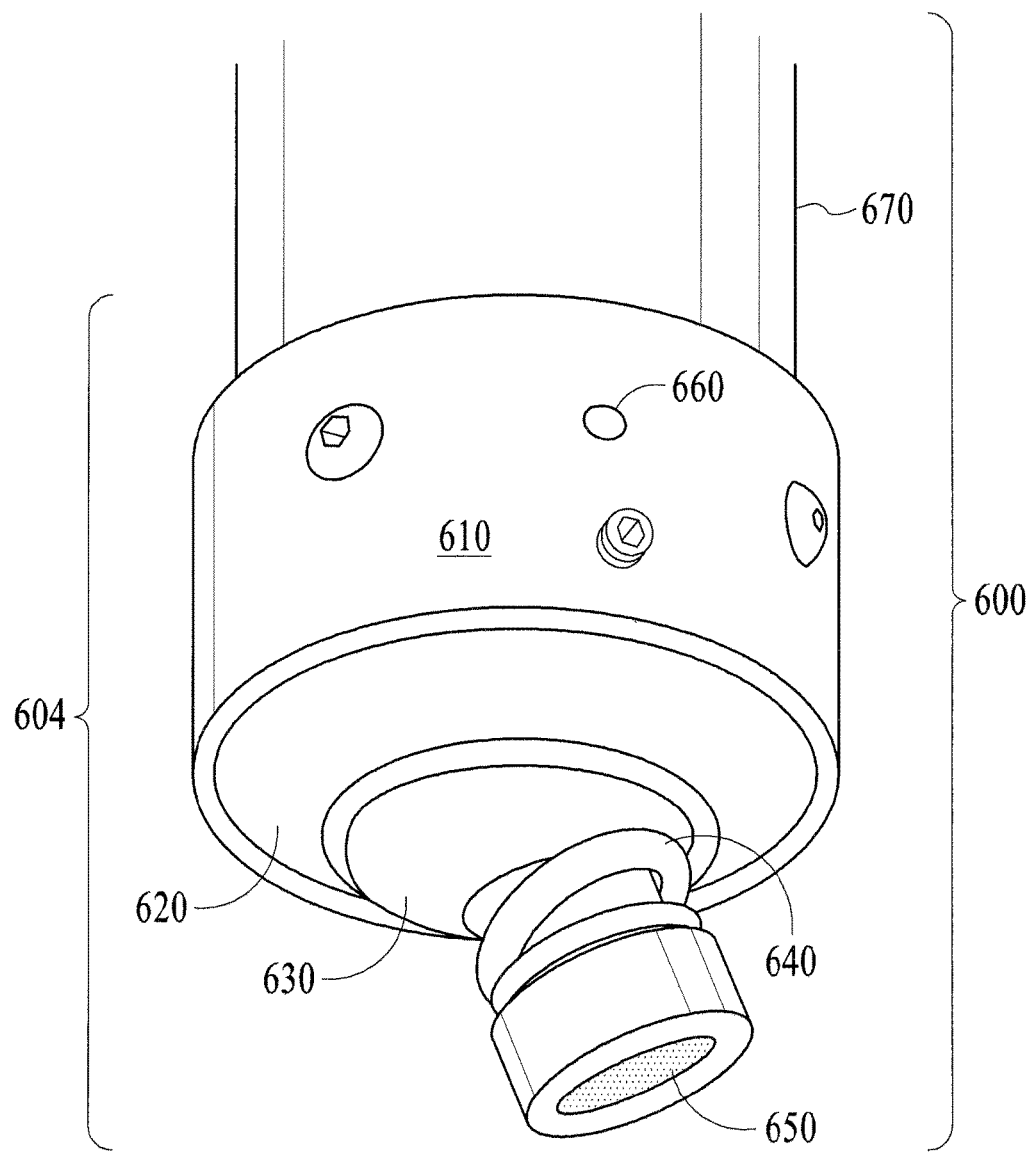
FIG. 8 illustrates a close-up of reader head showing pivot flexibility for reading on non-level surfaces, and also showing quick-drain holes.

The photograph in FIG. 8 illustrates the bottom 604 of the reader head assembly 600 with variable angle foot 610, 620, 630, 640 650 with quick drain holes 660 for product that ingresses into staff 500 and the reader head cylinder 670 to drain out of the system. The attachment mount 610 holding the swivel joint 620, 630 with spring 640 and UT sensor probe head 650.

Figure 9:
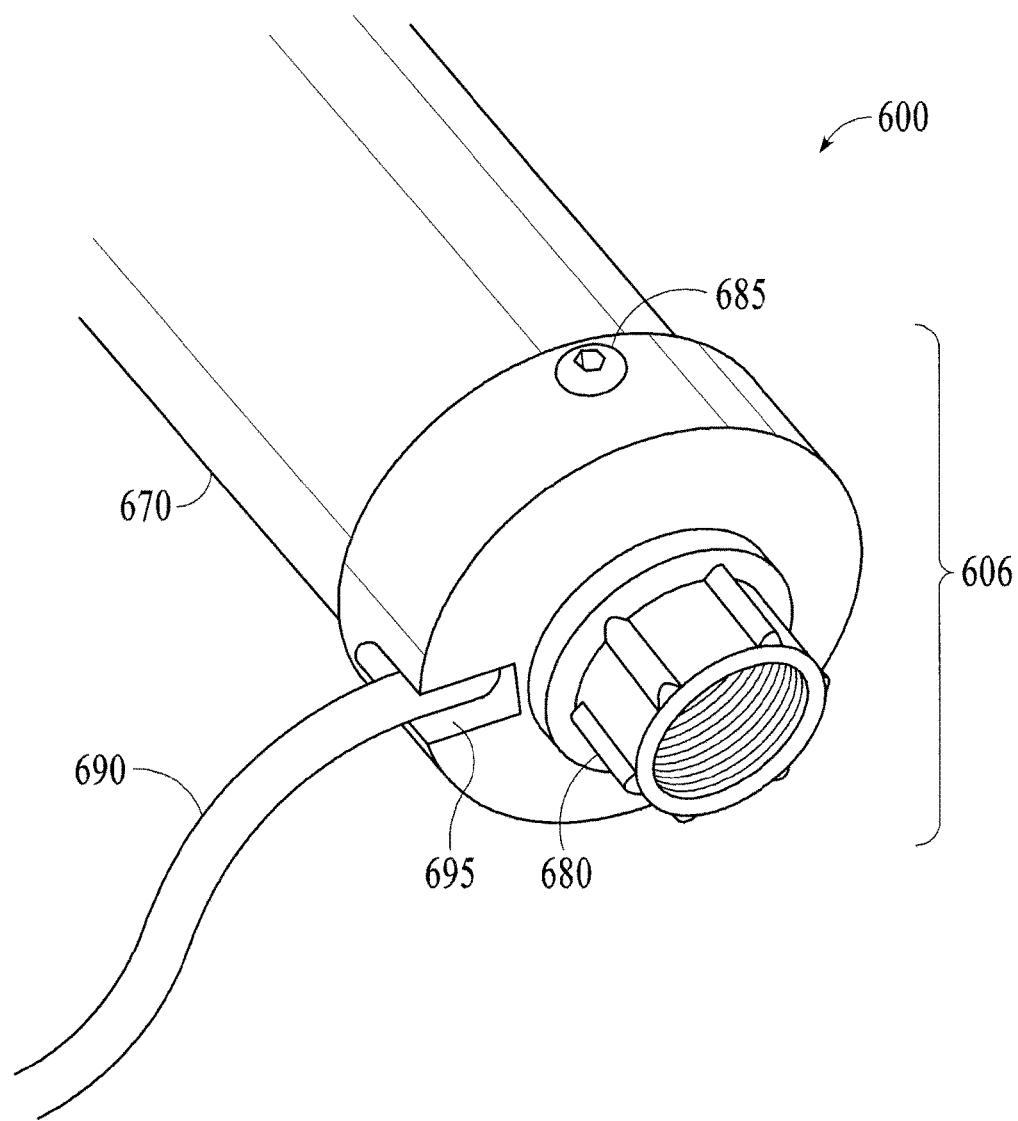

The photograph in FIG. 9 illustrates the top 606 of the read head assembly 600 showing the reach arm connection 680, the sensor cable 690 and cable pass-through 695, and the connector 685.

Figure 10:
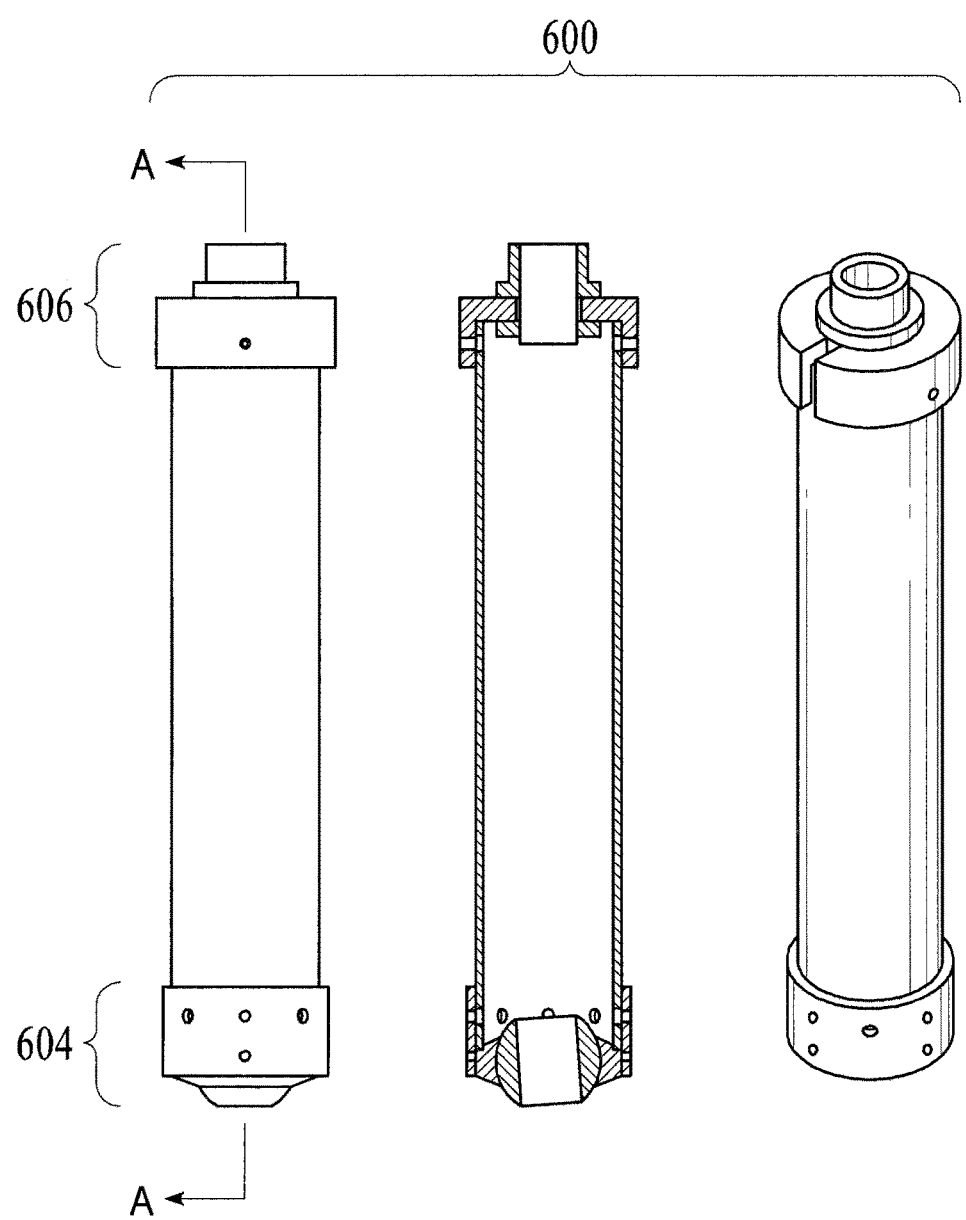
FIG. 10 illustrates an Assembly drawing of the in-tank UT reader unit.

FIG. 10 illustrates an assembling drawing of the reader head 600 and top 606 and bottom 604 of the reader head illustrated in FIGS. 8 and 9.

Figure 11:
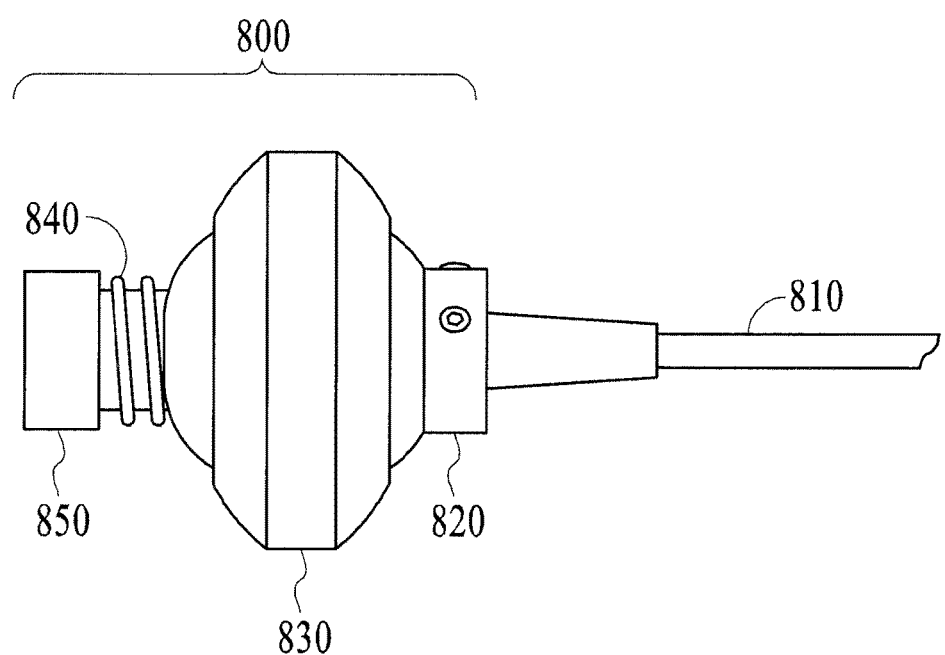
FIG. 11 illustrates the assembly of UT sensor, spring, swivel joint, and shaft collar.

The photograph in FIG. 11 illustrates a more detailed photograph of the inside assembly of the reader head cylinder 600 comprising the UT sensor 850, swivel joint 830 and spring 840, the shaft collar 820, and the cable 810 leading to the UT sensor 850.

Some additional features of the UT sensor system illustrated in FIGS. 6-11 are summarized below:

The intrinsically safe extended reach measurement arm as seen in the figures is comprised of an ultrasonic thickness gage on a swivel mount with a slack cable space and reach arm connection allowing reach across variable depth and angle with ability to interface with surfaces at an angle to the reach axis.

The unit is capable of operating within liquid conditions as illustrated in FIG. 6.

Able to operate across varying distances as illustrated in FIG. 7.

The swivel joint illustrated in FIGS. 8-11 allows for operation at an angle with respect to the surface being measured.

The cap illustrated in FIGS. 9 and 10 allows for extension attachment and cable routing from slack tube.

The slack tube illustrated in FIGS. 7-11 allows for sufficient cable slack for swivel operation while preventing cable mass dragging the swivel off normal to the measurement surface.

The UT sensor illustrated in FIGS. 8, 9, and 10 is mounted so that the swivel allows it exclusive contact to the surface of interest for measurements.

Figure 12:
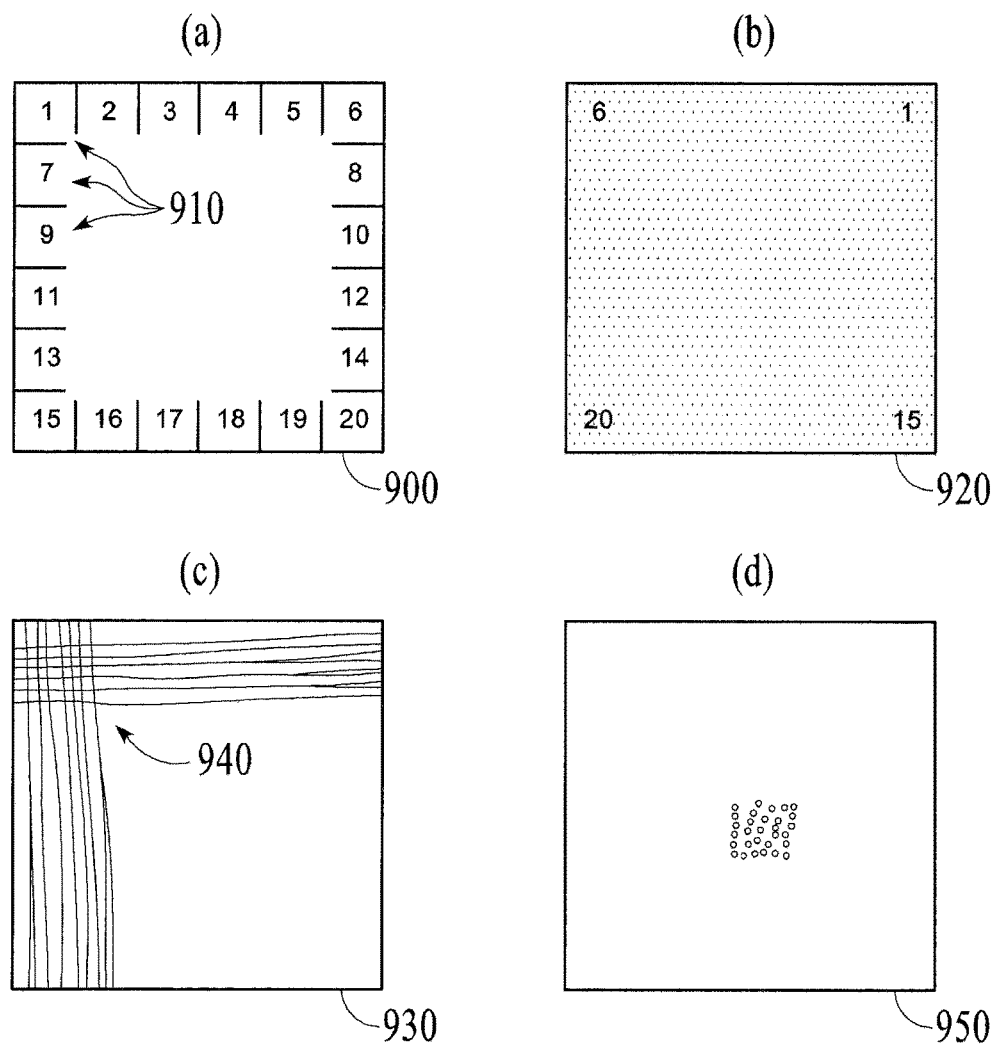
FIG. 12 illustrates the measurements of the precision and accuracy of the UT sensor was made in air and submerged in water on a variety of surfaces like those illustrate above.

Measurements of the precision and accuracy of the UT sensor were made on 4 types of coupons to verify that accurate measurements of the thickness of the steel plate comprising the floor of a steel tank for various types of bottom conditions. The photographs in FIG. 12 illustrates the four coupons used. FIG. 12*a* illustrates a 0.25-in. steel coupon with measurements made at 20 locations around the edge of the coupon. This illustrates a tank with a clean steel surface and uniform corrosion. FIG. 12*b* illustrates a 0.25-in. coupon that was coated with epoxy with a coating thickness greater than 0.10 in. This illustrates a tank that has been lined with a coating. FIGS. 12 *c* and 12 *d* illustrate heavily damaged floor conditions. FIG. 12*c* illustrates a 0.25-in. steel coupon with $\frac{1}{64}$- to $\frac{1}{32}$-in. deep grooves spaced at $\frac{1}{8}$ in., and FIG. 12 *d* illustrate a region in the steel plate containing $\frac{1}{16}$-in.-diameter holes in the steel coupon. In all cases, the mean measurements of thickness were within 0.01 in. of the actual coupon thickness measured with a precision caliper to the nearest 0.001 in.

Measurements with the UT and AE corrosion activity test sensor systems were made in a 60-ft diameter AST containing diesel fuel. Six 6 UT measurements indicated a bottom thickness of 0.0239 in. and a corrosion rate over the last 8 years of 1.3 mpy. The results of the AE corrosion activity test showed no corrosion activity in the tank.

While certain representative embodiments and details have been shown for purposes of illustrating the invention, it will be apparent to those skilled in the art that various changes in the methods and apparatus disclosed herein may be made without departing from the scope of the invention which is defined in the appended claims.

What is claimed is:

1. A method for determining the local thickness of the floor of an in-service steel liquid product tank comprising the steps of:
    (a) mounting an ultrasonic transducer thickness measurement sensor (UT sensor) on the end of a staff;
    (b) inserting the UT sensor into a liquid product in said tank from an opening in the top of said tank;
    (c) placing the sensor directly on or near the floor of said tank without taking said tank out-of-service;
    (d) taking ultrasonic measurements of the floor using the UT sensor; and
    (e) computing the local thickness of the floor using the ultrasonic measurements, where said computed floor thickness is used to calculate a corrosion rate, comprising the steps of (i) subtracting the computed floor thickness from a previous measurement of floor thickness made in the same local region or in a region representative of the same local region at an earlier time to determine a change in thickness; and (ii) dividing said change in thickness by the time between the two measurements.

2. The method of claim 1, where said UT sensor comprises a swivel joint that allows said floor thickness measurements to be made when the UT sensor head is not perpendicular to the floor during said floor thickness measurements.

3. The method of claim 1, where said UT sensor comprises a cable cylinder that provides sufficient cable length to allow movement of said UT sensor.

4. The method of claim 1, where said corrosion rate is used to compute a probability distribution indicating the life expectancy of the tank based on when said floor of said tank reaches a minimum allowable thickness in at least one location, where said floor thickness can be determined from a multiplicity of said floor thickness measurements and where said minimum allowable thickness can be near or at zero based on a relationship between tank age and corrosion rate.

5. The method of claim 4, where the time to the next complete internal inspection of said floor or of said tank is determined from said survival probability distribution and an updated survival probability distribution based on a Bayesian estimate given the age of said tank, and the knowledge that said tank at said age has survived and has remaining life.

6. The method of claim 5, where said time to the next complete internal inspection of said floor of said tank is computed by computing the equivalent risk time interval, which is computed from the future age of said tank when the probability of survival based on said Bayesian probability distribution is the same as the probability of survival based on said survival probability distribution.

7. The method of claim 6, where said knowledge that said tank at said age has survived and has remaining life is determined from a passing result of a leak detection test.

8. The method of claim 5, where said knowledge that said tank at said age has survived and has remaining life is determined from a passing result of a leak detection test.

9. A method for determining the local thickness of the floor of an in-service steel liquid product tank comprising the steps of:
    (a) mounting an ultrasonic transducer thickness measurement sensor (UT sensor) on the end of a staff;

(b) inserting the UT sensor into a liquid product in said tank from an opening in the top of said tank;

(c) placing the sensor directly on or near the floor of said tank without taking said tank out-of-service;

(d) taking ultrasonic measurements of the floor using the UT sensor; and (e) computing the local thickness of the floor using the ultrasonic measurements, where said local measurement of floor thickness is used to estimate said floor thickness over the entire floor using data selected from the group consisting of (i) the results of an acoustic emission test of corrosion activity where the result of said corrosion activity test indicates little to no corrosion of said floor of said tank, (ii) the results from updating the floor thickness measurements made and reported in previous internal inspections of said floor thickness reported in previous out-of-service internal inspections of said floor, and (iii) previous robotic inspection of said floor thickness of said tank with said local measurement of floor thickness.

10. The method of claim 9, where said local measurement of floor thickness is used to estimate said floor thickness over the entire floor by using and combining the results of an acoustic emission test of corrosion activity where the result of said corrosion activity test indicates little to no corrosion of said floor of said tank and the results of said floor thickness measurements from a previous out-of-service internal inspection of said floor after updating said previous inspection results with said local measurement of floor thickness.

11. The method of claim 9, where said local measurement of floor thickness is used to estimate said floor thickness over the entire floor by using and combining the results of an acoustic emission test of corrosion activity where the result of said corrosion activity test indicates little to no corrosion of said floor of said tank and the results of said floor thickness measurements from a previous robotic inspection of the said floor thickness of said tank with said local measurement of floor thickness.

12. The method of claim 9, where said UT sensor is replaced by another floor thickness sensor capable of measuring said floor thickness, said sensor selected from the group consisting of magnetic flux sensors and long range ultrasonic transducers (LRUT).

13. The method of claim 9, where said floor thickness measured with said floor thickness measurement sensor is used to compute the corrosion rate, comprising the steps of:

(a) measuring the thickness of said floor with said floor thickness measurement sensor;

(b) subtracting said thickness from a previous measurement of floor thickness made at said local region or a region representative of said local region at an earlier time; and (c) dividing said change in thickness by said difference in time determined from said time of said measurement and said earlier time.

14. The method of claim 9, where said floor thickness measurement is used to compute the time between or the time to the next complete internal inspection of said floor or said tank when the floor of said tank reaches a minimum allowable thickness in at least one location in said tank, where said floor thickness can be determined from a multiplicity of said floor thickness measurements and where said minimum allowable thickness can be near or at zero, comprising the steps of:

(a) computing the difference in said thickness of said tank floor and said minimum allowable thickness;

(b) dividing said difference by a corrosion rate calculated by (i) subtracting the computed floor thickness from a previous measurement of floor thickness made in the same local region or in a region representative of the same local region at an earlier time to determine a change in thickness; and (ii) dividing said change in thickness by the time between the two measurements.

15. The method of claim 13, where said corrosion rate is used to compute a probability distribution indicating the life expectancy (or survival) of a tank based on when said floor of said tank reaches a minimum allowable thickness in at least one location in said tank, where said floor thickness can be determined from a multiplicity of said floor thickness measurements and where said minimum allowable thickness can be near or at zero based on a relationship between tank age and corrosion rate.

16. The method of claim 15, where the time between or the time to the next complete internal inspection of said floor or said tank is determined from said survival probability distribution and an updated survival probability distribution based on a Bayesian estimate given the age of said tank, the knowledge that said tank at said age has survived and has remaining life.

17. The method of claim 16, where said time between or to the next complete internal inspection of said floor or said tank is computed by computing the equivalent risk time interval, which is computed from the future age of said tank when the probability of survival based on said Bayesian probability distribution is the same as the probability of survival based on said survival probability distribution.

18. The method of claim 16, where said knowledge that said tank at said age has survived and has remaining life is determined from a passing result of a leak detection test.

19. The method of claim 17, where said knowledge that said tank at said age has survived and has remaining life is determined from a passing result of a leak detection test.

20. The method of claim 9, where said AE corrosion activity test is performed with one or more AE sensors mounted at different locations on the external shell of said aboveground storage tank such the corrosion activity acoustic signal from each corrosion activity event is detected with each AE sensor.

21. The method of claim 20, where said AE sensor array is comprised of two or more sensor located at different locations on said shell of said tank corrosion activity test is performed with two or more AE sensors mounted on the external shell of said tank.

22. The method of claim 21, where said AE sensors are mounted around the entire circumference of the shell.

23. The method of claim 21, where three AE sensors at different locations are used with two of the AE sensors at one elevation and the other AE sensor at a different elevation but vertically above one of the other sensors.

24. The method of claim 21, where four AE sensors at different locations are used with two of the AE sensors at one elevation and the other AE sensor at a different elevation but vertically above one of the other sensors such that the four sensors are located at the following Cartesian coordinates: (0,0), (0, x1), (0,y1), and (0,z1) where 0 can be at any location on the shell.

25. The method of claim 21, where said sensors are located on the shell at the same approximately elevation.

26. The method of claim 25, where said sensors use the time of arrival of said corrosion activity at two or more AE sensors to triangulate back to the location of said corrosion activity signal.

27. The method of claim 25, where such triangulation verifies the presence of a corrosion activity signal.

28. The method of claim 25, where such triangulation is used to locate each of said corrosion activity signals.

29. The method of claim 25, where at least one of said AE sensors are located at a different elevation.

30. The method of claim 29, where said AE sensors are used to differentiate false signals from the surface for corrosion activity signals from said tank floor.

31. The method of claim 9, where the results of an AE corrosion activity test indicate no or minimal active corrosion through the tank and said measurement of tank floor thickness and said corrosion rate is assumed to be representative of the entire tank floor.

32. The method of claim 9, where said AE corrosion activity test is performed with one or more AE sensors are submerged in the fluid in said tank and are mounted at different locations in said tank, either said aboveground or said underground storage tank such that the corrosion activity acoustic signal from each corrosion activity event is detected with each AE sensor.

33. The method of claim 32, where said AE sensor array is comprised of two or more sensors.

34. The method of claim 33, where said sensors are located at the same approximate elevation.

35. The method of claim 34, where said sensors use the time of arrival of said corrosion activity at two or more AE sensors to triangulate back to the location of said corrosion activity signal.

36. The method of claim 35, where such triangulation verifies the presence of a corrosion activity signal.

37. The method of claim 35, where such triangulation is used to locate each of said corrosion activity signals.

38. The method of claim 34, where at least one of said AE sensors are located at a different elevation.

39. The method of claim 38, where said AE sensors are used to differentiate false signals from the surface for corrosion activity signals from said tank floor.

40. The method of 32, where three AE sensors at different locations are used with two of the AE sensors at one elevation and the other AE sensor at a different elevation but vertically above one of the other sensors.

41. The method of 32, where three AE sensors at different locations are used with two of the AE sensors at one elevation and the other AE sensor at a different elevation but vertically above one of the other sensors such that the four sensors are located at the following Cartesian coordinates: (0,0), (0, x1), (0,y1), and (0,z1) where 0 can be at any location within said tank.

42. The method of claim 32, where said submerged sensors are mounted on a vertical staff.

43. The method of claim 32, where said submerged sensors are suspended from the top of said tank.

44. The method of claim 32, where the results of an AE corrosion activity test indicate no or minimal active corrosion through the tank and said measurement of tank floor thickness and said corrosion rate is assumed to be representative of the entire tank floor.

45. The method of claim 9, where said UT sensor comprises a swivel joint that allows said floor thickness measurements to be made when the UT sensor head is not perpendicular to the floor during said floor thickness measurements.

46. The method of claim 9, where said UT sensor comprises a cable cylinder that provides sufficient cable length to allow movement of said UT sensor.

* * * * *